(12) United States Patent
Snyder et al.

(10) Patent No.: US 8,211,152 B2
(45) Date of Patent: *Jul. 3, 2012

(54) TENSION FIXATION SYSTEM

(75) Inventors: Brian D. Snyder, Westwood, MA (US);
Edward J. Vresilovic, Ardmore, PA (US); Hemal P. Mehta, Clarksville, TN (US); John A. Muller, Boston, MA (US)

(73) Assignee: Mass Modular Spine Group, Inc., Westwood, MA (US)

( * ) Notice: Subject to any disclaimer, the term of this patent is extended or adjusted under 35 U.S.C. 154(b) by 1035 days.

This patent is subject to a terminal disclaimer.

(21) Appl. No.: 12/039,128

(22) Filed: Feb. 28, 2008

(65) Prior Publication Data
US 2008/0221621 A1  Sep. 11, 2008

Related U.S. Application Data

(60) Provisional application No. 60/892,000, filed on Feb. 28, 2007.

(51) Int. Cl.
*A61B 17/70* (2006.01)
(52) U.S. Cl. .......................... 606/267; 606/264
(58) Field of Classification Search .................. 606/60, 606/246, 261, 264, 265, 267, 272, 300, 301, 606/305–308
See application file for complete search history.

(56) References Cited

U.S. PATENT DOCUMENTS

| | | | |
|---|---|---|---|
| 5,176,680 A | 1/1993 | Vignaud et al. | |
| 5,545,166 A | 8/1996 | Howland | |
| 5,716,415 A | 2/1998 | Steffee | |
| 6,325,802 B1 | 12/2001 | Frigg | |
| 6,869,433 B2 | 3/2005 | Glascott | |
| 7,785,352 B2 * | 8/2010 | Snyder et al. | 606/263 |
| 2004/0133140 A1 | 7/2004 | Aduana et al. | |
| 2005/0049589 A1 | 3/2005 | Jackson | |
| 2005/0177154 A1 | 8/2005 | Moumene et al. | |
| 2005/0277931 A1 | 12/2005 | Sweeney et al. | |
| 2007/0043356 A1 | 2/2007 | Timm et al. | |
| 2008/0051789 A1 * | 2/2008 | Snyder et al. | 606/61 |

* cited by examiner

*Primary Examiner* — Eduardo C Robert
*Assistant Examiner* — Ellen C Hammond
(74) *Attorney, Agent, or Firm* — Volpe and Koenig, P.C.

(57) ABSTRACT

The present invention provides an apparatus and method for fixation of a bone anchor to a structural member used for spinal fixation, whereby spinal deformity can be corrected and mechanical stability of the spine is provided so that load is carried fully or partially through the structural member. This invention provides fixation of a bone anchor to a structural member through tensile loading of a component of the fixation mechanism. This invention is widely adaptable to a variety of bone anchors and structural members. This invention allows reduction of spine deformity resulting from varied spinal disease through the fixation mechanism alone without the need for added reduction instrumentation systems. This invention equally provides a fixation mechanism for fixation of a bone anchor to the structural member of a spine fixation system in the absence of deformity.

20 Claims, 25 Drawing Sheets

TENSION FIXATION SYSTEM

BACKGROUND OF THE INVENTION

1. Field of the Invention

The invention relates to apparatus and methods for treating spinal disorders. More particularly, the invention relates to spinal fixation systems.

2. Summary of the Related Art

The human spine is a system of articulated vertebral segments with tissues including vertebrae, intervertebral discs, facet joints, ligaments, and muscles. The human spine generally includes 24 vertebrae and the sacrum. These 24 vertebrae are designated from the head to the pelvis (cervical, thoracic, lumbar, and sacral). There are 7 cervical vertebrae, 12 thoracic vertebrae, 5 lumbar vertebrae (although this number may vary from 4 to 6 lumbar vertebrae in some humans), and 4 sacral vertebrae. The spine generally includes 25 articulations; each bone articulates with the one above and below. The superior C1 vertebra articulates with the skull and the inferior L5 vertebra articulates with the sacrum. With two exceptions, articulations between the vertebrae are through intervertebral discs and bilateral facet joints. The exceptions are the occipital-C1 and C1-C2 articulations. In addition to the vertebral discs and facet joints, other structural elements of the vertebrae include ligaments which connect and allow constrained mobility of the vertebrae, and musculature attachments through tendons to fixation points on the vertebrae to allow motion and maintain stability. The spine functions mechanically to protect the neurological elements of the spinal cord, to bear load and maintain posture, and to allow motion of the trunk and neck. Failure of any structural components of the spine as a result of disease or injury may lead to loss of the mechanical integrity of the spine, which may lead to neurological injury, mechanical instability, and deformity.

Loss of mechanical integrity of the spine may result from congenital or developmental abnormality, metabolic disorder, tumor, infection, trauma, arthritis, and degenerative disc disease or injury to any of the functional units of the spine, including vertebrae, intervertebral discs, facet joints, ligaments, and muscles. Ultimately, this can lead to pain, loss of function, and/or neurological impairment.

One of the main treatment modalities for loss of mechanical integrity of the spine has been the use of spinal fixation systems. These systems function to restore the mechanical integrity of the spine, by improving spine stability and correcting deformity.

A typical spinal fixation system includes 2 primary components: bone anchors and structural members. Bone anchors allow mechanical connection to vertebrae and may include, but are not limited to, such fixation means as screws, hooks, wires, and clips. Structural members allow interconnection between the bone anchors and they include, but are not limited to, such objects as rods or plates. The strategies for correcting mechanical instability and spinal deformity are varied, but typically allow for multiple points of fixation to the spine above and below the unstable segments or areas of deformity. Structural members are attached to these multiple points of spine fixation to the spine, providing mechanical stability and/or correction of deformity by supporting load and transmitting corrective forces and moments.

The bone anchors are fixed to the structural members using a variety of mechanical mechanisms. Early constructs were generally limited to bone anchor fixation points at the ends of the structural member. These bone anchors commonly used fixed capturing on the structural members by passing the structural member though the bone anchor and fixing the anchor to the spine while captured. However, these constructs were limited in their ability to correct deformity as they were limited by the amount of force and moment, which could be imparted to the spine though a single bone anchor at the end of a structural member. This limitation gave rise to segmental fixation systems, which allow larger corrective forces and moments to be applied to the spine because of multiple points of spine fixation through the use of multiple bone anchors. The attachment of the structural member to multiple bone anchors has required a mechanical mechanism for attaching the bone anchors to the structural member after placement of the bone anchors. This has all but eliminated fixed capture bone anchors.

Current systems use dynamic capture mechanisms for attaching the structural member to the bone anchors. A variety of mechanisms have been disclosed where dynamic capture has been based on the principle of the screw thread fixation; for example, U.S. Pat. No. 5,176,680 discloses a device for fixing a spinal rod to vertebral screws, in which a spinal rod is passed through a split ring which is positioned between the prongs of a vertebral screw having a forked head. This assembly is locked into place by a locking screw threaded between the prongs of the forked head and onto the split ring. Similarly, U.S. Pat. No. 5,545,166 discloses a spinal fixation system that includes a plurality of anchor screws, clamp assemblies, pivot blocks, clamp blocks and rods that are implanted along a patient's spine to fix two or more adjacent vertebrae relative to each other. U.S. Pat. No. 5,716,415 discloses a spinal implant having upper and lower surfaces that include a plurality of triangular-shaped teeth that extend from the side surface to the side surface for engaging the vertebrae. U.S. Pat. No. 6,869,433 discloses a polyaxial screw assembly comprising a screw having cancellous threads for insertion into the cancellous bone of a vertebra, especially through the pedicle. A spherically shaped head has a convex surface and a tool recess for receiving a hex driver or other tool. The head is received within a tubular receiver having an internal concave surface and an adjacent opening. The convex surface of the head mates with the concave surface. The opening is smaller than the head so that the screw can project out of the opening without falling out of the receiver. A pressure disk sits atop the head and has a surface of mating shape to that of the head. The receiver also has a U-shaped portion which receives an elongated rod. The rod is used to connect adjoining vertebrae. An internal nut and external nut compress the rod against the pressure disk which in turn compresses the head convex portion into the receiver concave portion and locks the angular position of the receiver with respect to the screw.

To correct spine deformity, the structural member must be attached to the bone anchors on the deformed spine or ribs. Two strategies or a combination are employed to effect correction. The first is to conform the structural member to the deformed spine and attach the bone anchors to the structural member. Then correcting the deformity by further contouring the structured member to the corrected conformation, compressing and/or distracting sequential bone anchors until the final corrected conformation of the spine is achieved. The second strategy is to set the structural member to the final corrected conformation of the spine and attach the bone anchors to the structural member, correcting the spine deformity at the time of attachment of the bone anchors. When the second strategy is employed, it requires the bone anchors to move to the structural member and to be attached to the structural member.

Currently, this second strategy of moving the bone anchors to the structural member for correction of deformity is accomplished using one of two techniques or a combination.

The first technique employs reduction instrumentation, which is not integral to the structural member or bone anchor. Reduction instrumentation applies forces to the spine via the bone anchor to move the spine and bone anchor to the structural member where it is attached once the deformity is reduced. Reduction instrumentation systems generally operate via a threaded screw-type reduction action, or a plier-like lever reduction action to bring the bone anchor to the structural member. While these reduction instrumentation systems may be used to good effect, they are space occupying, commonly cumbersome, and frequently time consuming in the confines of a surgical wound, which is already filled with the bone anchors and the structural members. Their use often leads to both increased wound size and operative time, which translate to potential increased operative morbidity given increased risks of prolonged anesthesia, bleeding, and infection.

The second technique employs bone anchors with reduction action integral to the anchor itself. The techniques of Luque, sub-laminar wire bone anchors, or Wisconsin Wiring, wire passed through the spinous process anchoring bone, where the spine is reduced to the structural member by twisting wires around the structural member, are examples of this second technique. While these techniques offer some advantages over reduction instrumentation techniques and are still used on a limited basis, they have lost favor for reasons of neurological risk associated with passing sub-laminar wires and issues concerning secure fixation to the structural member. Another example of this technique is the use of long posted pedicle screws.

Such long posted pedicle screws allow a certain degree of movement of the bone anchor to the structural member by using an extended anchor-structural member fixation mechanism to facilitate movement of the anchor to the structural member. Once the structural member is captured by the fixation nut on the long posted pedicle screw, drawing the nut down moves the anchor until it is fixed on the structural member. Practically, this requires movement of the anchor in a plane that is defined by the axis of the screw and the tangent to the structural member at the point of fixation. For a single screw this is not severely limiting, but for two or more screws, this condition gives rise to multiple planes of bone anchor movement which must remain intersected at the structural member through the reduction process, a condition which can only be met by one plane provided that the starting holes for the multiple pedicle screws define a plane that contains all the individual pedicle screw longitudinal axes. This relatively severe limitation generally requires that a single long posted screw anchor be solely loaded at the reduction of deformity, which increases the risk of failure of both the reduction and the anchor.

Thus, there is a need for a bone anchor fixation mechanism, which can serve as a reduction device, is widely applicable to a variety of bone anchors beyond long posted pedicle screws and does not impose severe restrictions on anchor placement. Such a mechanism offers significant advantages for correction of spine deformity and ease of use, which would translate into improvement in patient care.

BRIEF SUMMARY OF THE INVENTION

The present invention provides an apparatus and method for fixation of a bone anchor to a structural member used for spinal fixation, whereby spinal deformity can be corrected and/or mechanical stability of the spine is provided so that load is carried fully or partially through the structural member. This invention provides fixation of a bone anchor to a structural member through tensile loading of a component of the fixation mechanism. This invention is widely adaptable to a variety of bone anchors and structural members. This invention allows reduction of spine deformity resulting from varied spinal disease through the fixation mechanism alone without the need for added reduction instrumentation systems. This invention equally provides a fixation mechanism for fixation of a bone anchor to the structural member of a spine fixation system in the absence of deformity.

BRIEF DESCRIPTION OF THE DRAWINGS

FIG. 6e shows that the connector base and tension strap may form a unitary body that is either rigid or flexible.

DETAILED DESCRIPTION OF THE PREFERRED EMBODIMENTS

The present invention provides an apparatus and method for fixation of a bone anchor to the structural member of a spine fixation system whereby the spine is provided mechanical stability and correction of deformity through load carried fully or partially through the structural member. This invention provides fixation of a bone anchor to a structural member through tensile loading of a component of the fixation mechanism. This invention is widely adaptable to a variety of bone anchors and structural members. This invention allows reduction of spine deformity resulting from varied spinal disease through the fixation mechanism alone without the need for added reduction instrumentation systems. This invention equally provides a fixation mechanism for fixation of a bone anchor to the structural member of a spine fixation system in the absence of deformity.

In a general sense, the invention provides an apparatus for fixation of a bone anchor of a spinal fixation system to a support element of the spinal fixation system, wherein the spinal fixation system comprises a plurality of fixation members connected by a support element, wherein each fixation member comprises an attachment member, a connector base attached thereto, a tension strap and a capture member, wherein the attachment member comprises attachment means for attachment to a vertebra and a docking member for attachment to the connector base; wherein the connector base comprises means for attachment to the docking member, a body, a ball-shaped member disposed within the body, and a channel disposed between the ball-shaped member and the body, wherein the tension strap passes through the channel and around the ball-shaped member and has upper sections that extend beyond the ball-shaped member for attachment to the capture member, wherein the capture member comprises a body having a lower surface and an upper surface, the body having a first set of holes therethrough for receiving the tension strap and a second hole containing a locking member; wherein the bone anchor in place in a vertebra is attached to the connector base which engages the tension strap in the channel formed between the connector base and the ball-shaped member, the capture member having holes through which the tension strap passes and providing compression against the structural member and being fixed into place by a cam lock, thereby applying tension to the tension strap and drawing down the structural member until it contacts the ball-shaped member at the base, thereby providing at least three points of fixation between the capture mechanism and the ball-shaped member of the base.

Figure 11A:
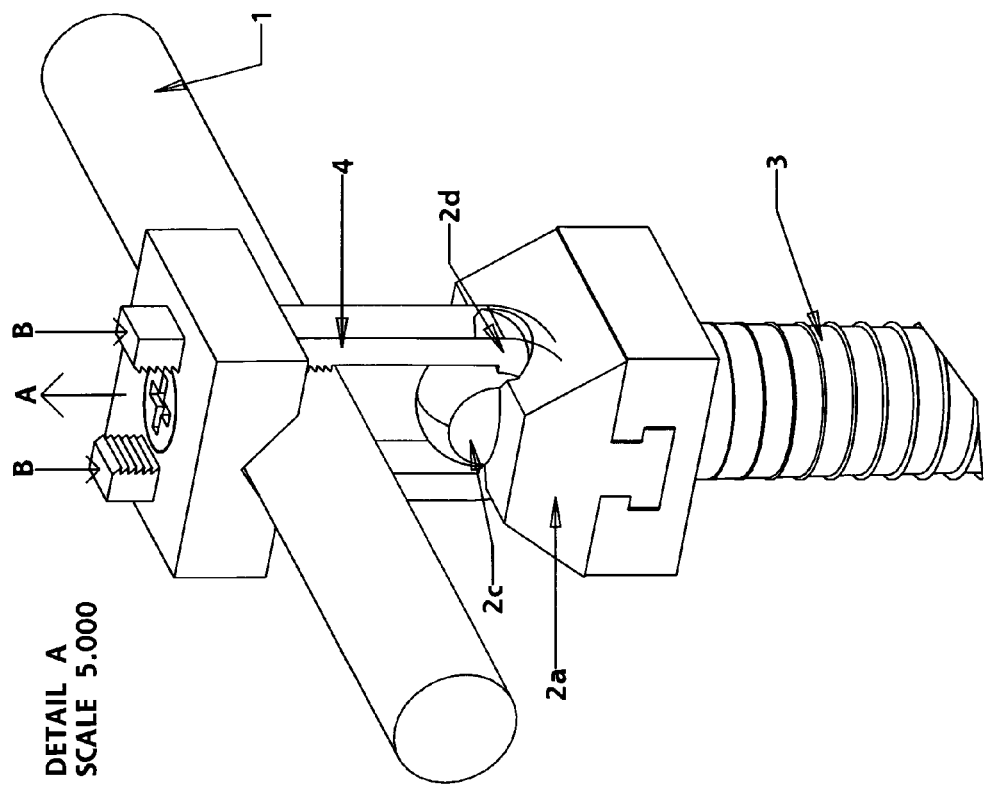
FIG. 11a shows rod reduction within the U-shaped strap, the strap being held within a channel (2d) formed between the capture member base (2a) and a ball-shaped member (2c). The top section of the capture member, as shown in FIG. 9a, is then drawn down under tension against the rod (1) over the U-shaped strap to form the final assembly, as shown in FIG. 11b (prior to trimming of the protruding ends of the U-shaped strap). Arrows A and B indicate, respectively, the direction of force on the capture member and tension strap.
Figure 11A:
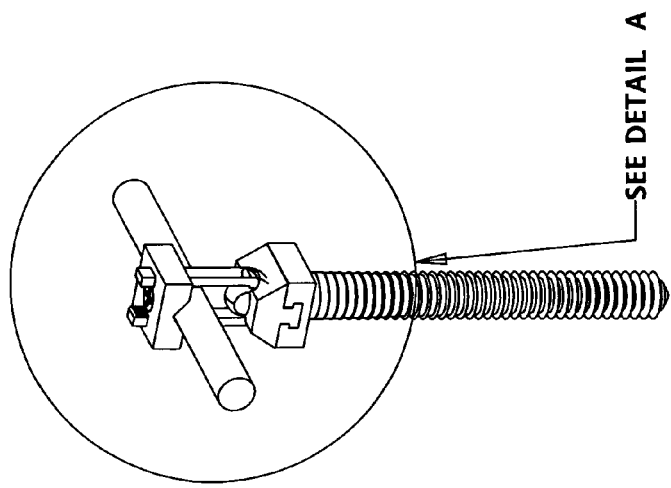
Figure 11B:
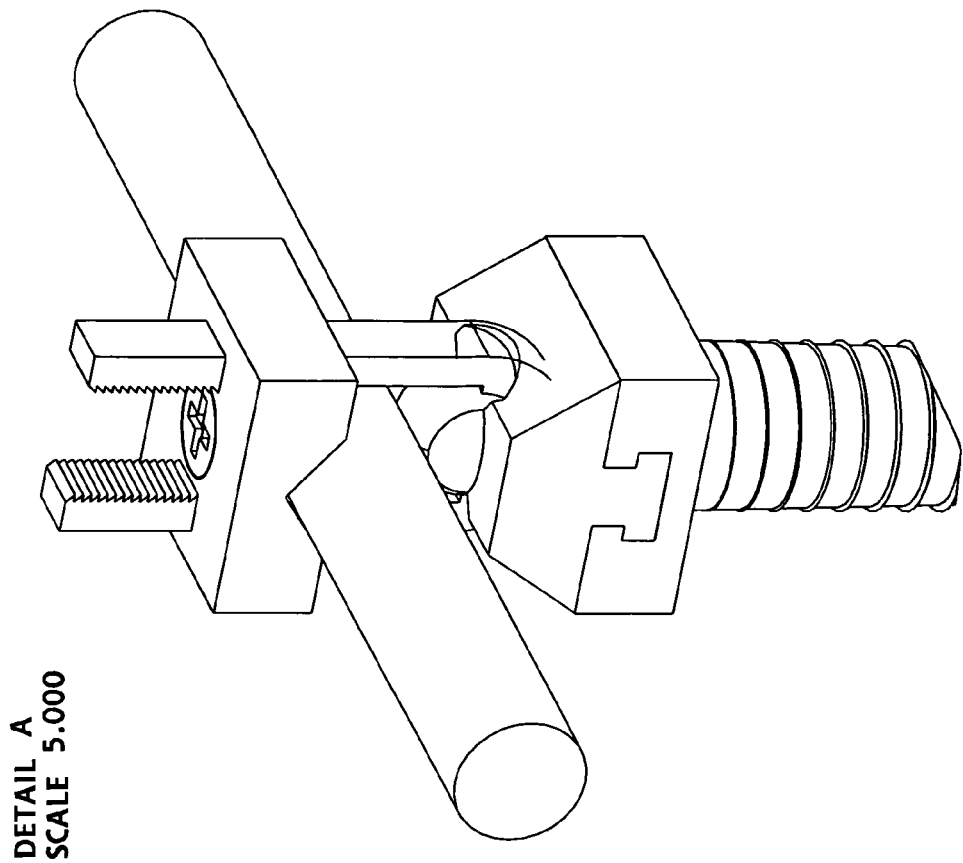
Figure 11B:
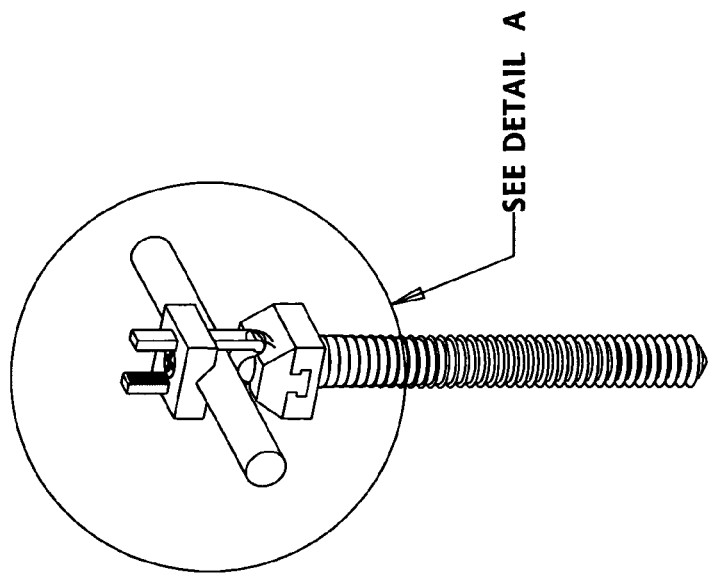

In a preferred embodiment of an apparatus for spinal fixation, the apparatus comprises, as shown in FIG. 11a, a bone anchor (3), (shown here as a bone screw) in place in a vertebra is attached to a connector base (2a) which engages a U-shaped tension strap (4) in a channel (2d) formed between the connector base and a ball-shaped member (2c). A capture member [FIG. 9a, (5)] having holes [FIG. 9a, (5d)] through which the U-shaped strap passes then provides compression against a structural member, shown in FIG. 11a as a rod (1) and is fixed into place with a cam lock [FIG. 9a, (5a)]. By applying tension to the U-shaped capture member, the structural member is drawn down until it contacts the ball-shaped member at the base. The V-wedge of the capture mechanism and the ball-shaped member of the base provide 3 points of fixation [FIG. 11b]. The protruding ends of the U-shaped strap are then trimmed. Alternatively, instead of a rod, the structural member can be a wire, or a beam element where the capture mechanism may or may not be integrated into the beam.

Figure 1:
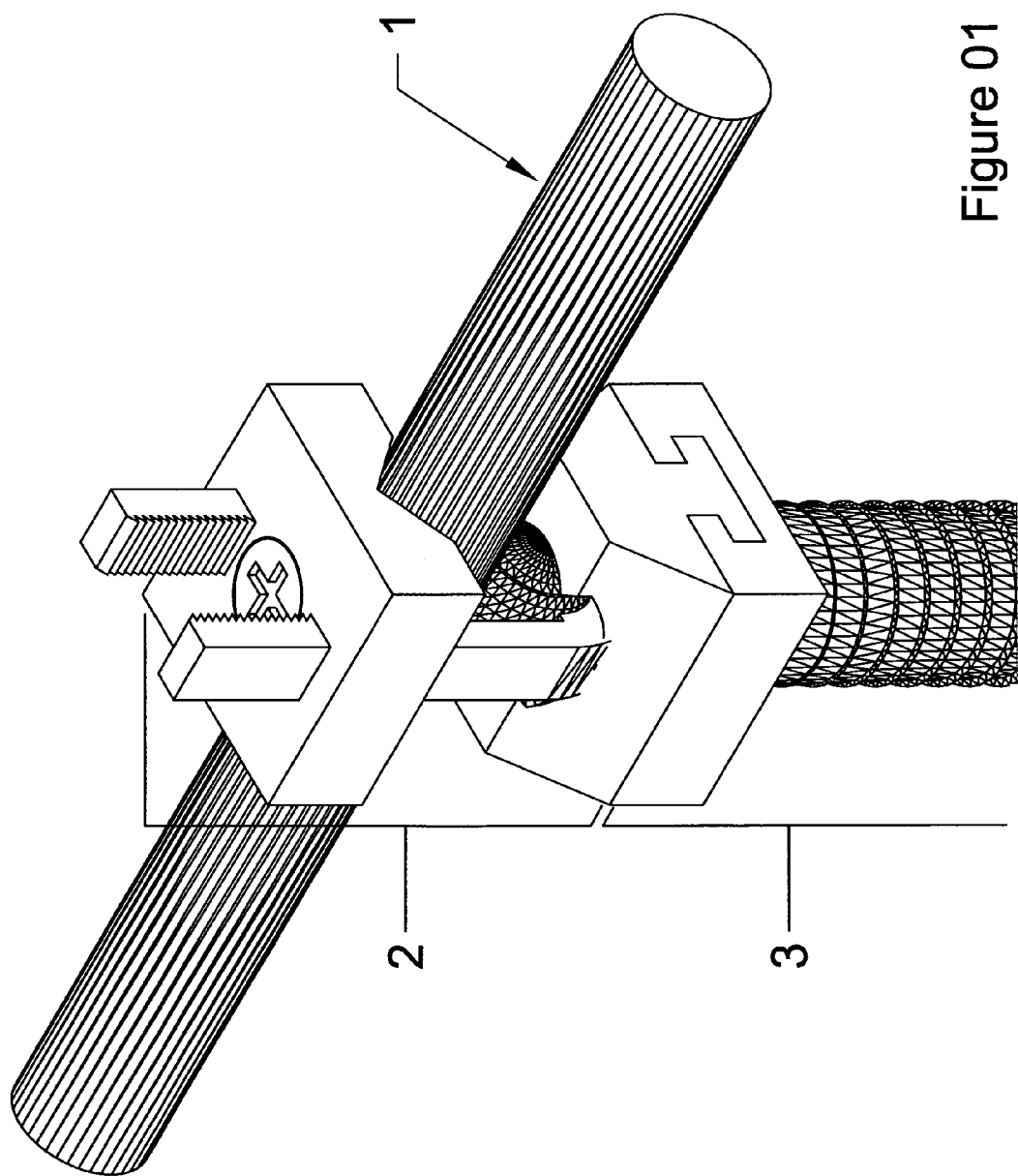
FIG. 1 shows a self-locking capture member in place over a structural connecting member, which in this embodiment is shown as a rod (1). The capture member (2) secures the rod to a vertebral attachment means, represented here by a bone screw (3).
Figure 2:
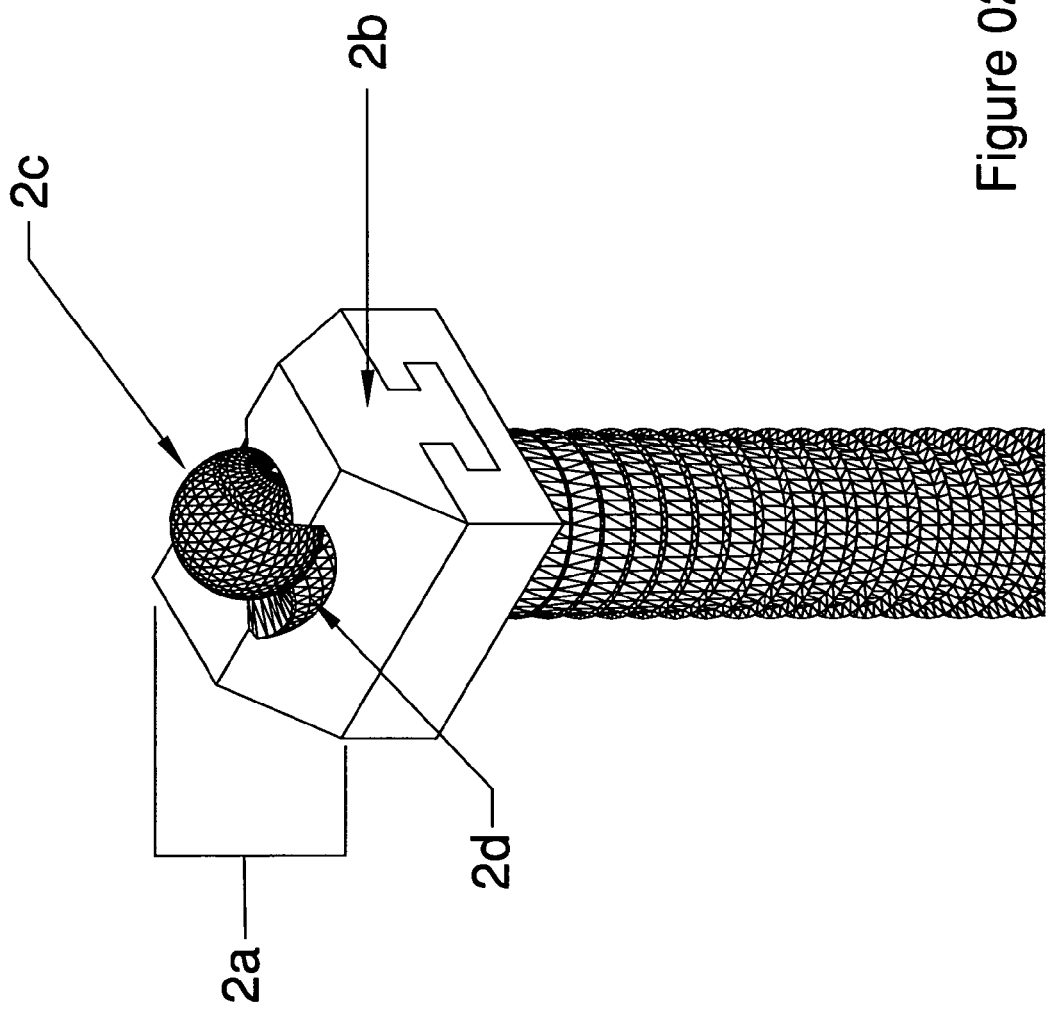
FIG. 2 shows the connector base component (2a) of the capture member, with a connector base body (2b), a ball-shaped member (2c), and a channel (2d) between the body and ball-shaped member.
Figure 3:
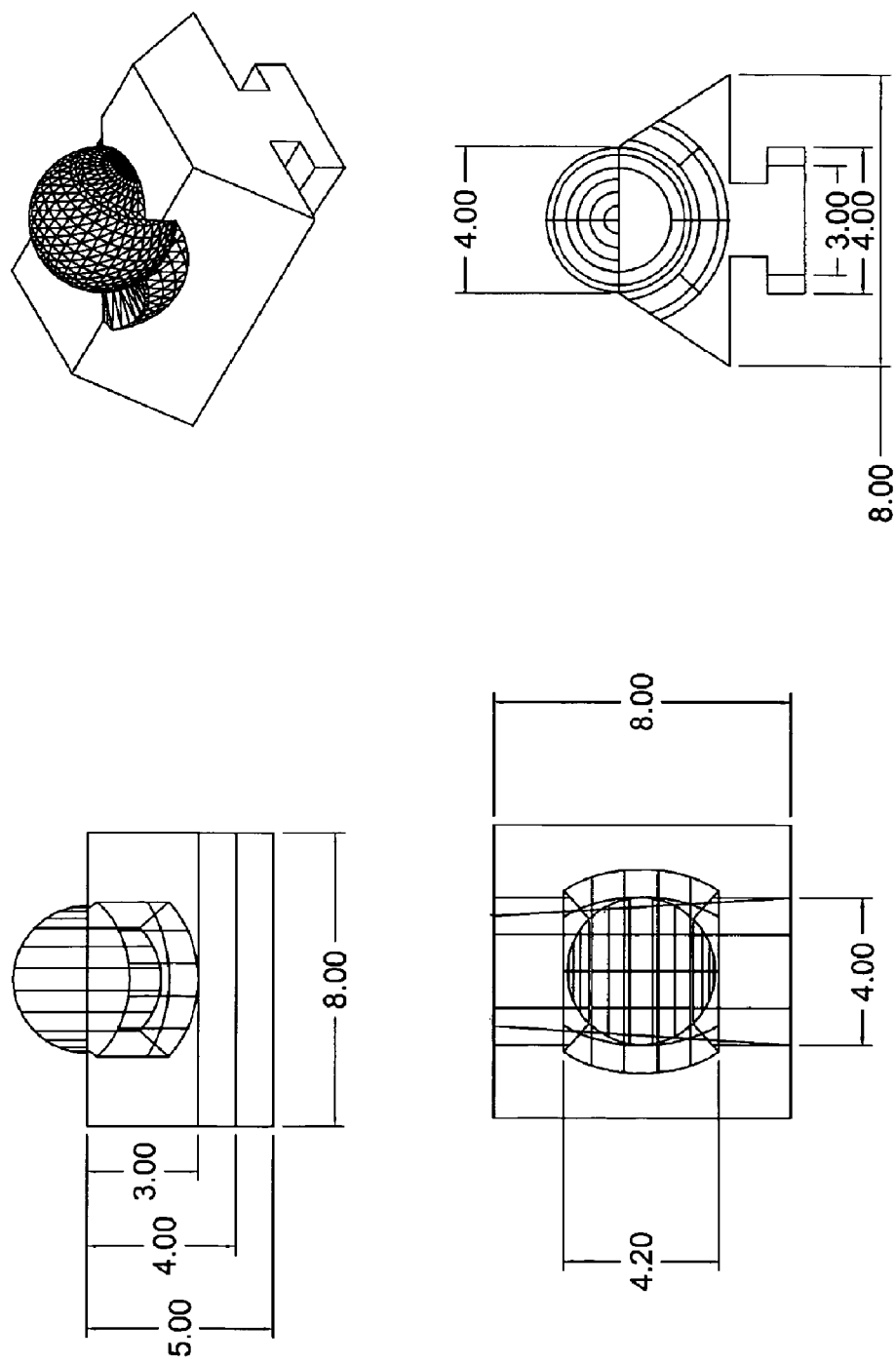
FIG. 3 shows various views of the connector base, including a side view, an isometric view, a top view, and a front view. The ball-shaped member (2c) shown in FIG. 3 has a spherical shape, which provides a constant radius between the rod (1) and the inner curve of a tension strap, such as the U-shaped strap (4) shown in FIG. 4. The connector base (2a) has a tapered foot, and includes a groove to accept and retain the tension strap.
Figure 4:
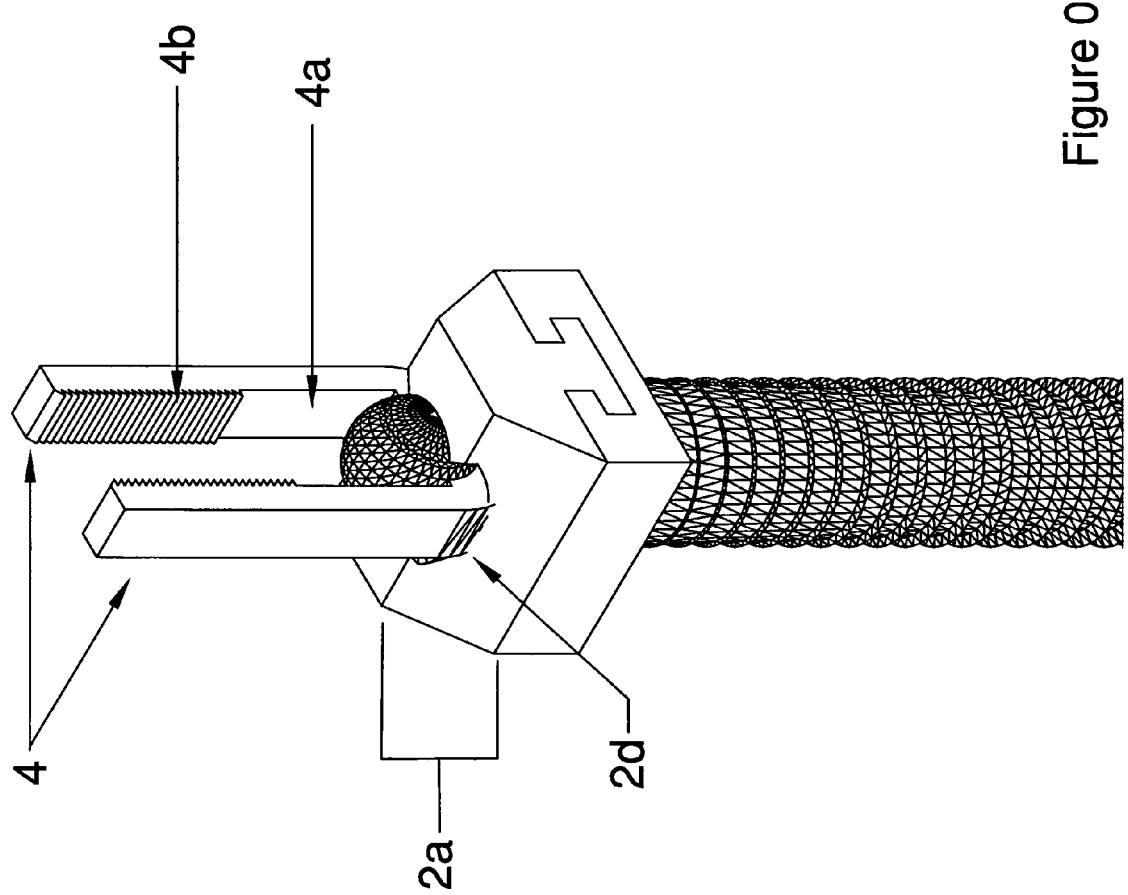
FIG. 4 shows the connector base (2a) with the tension strap in place, shown here as a U-shaped strap (4) placed in the channel (2d). As shown in this embodiment, the U-shaped strap has a smooth portion (4a) for passage through the channel, and a portion having a plurality of transverse ridges (4b).
Figure 5:
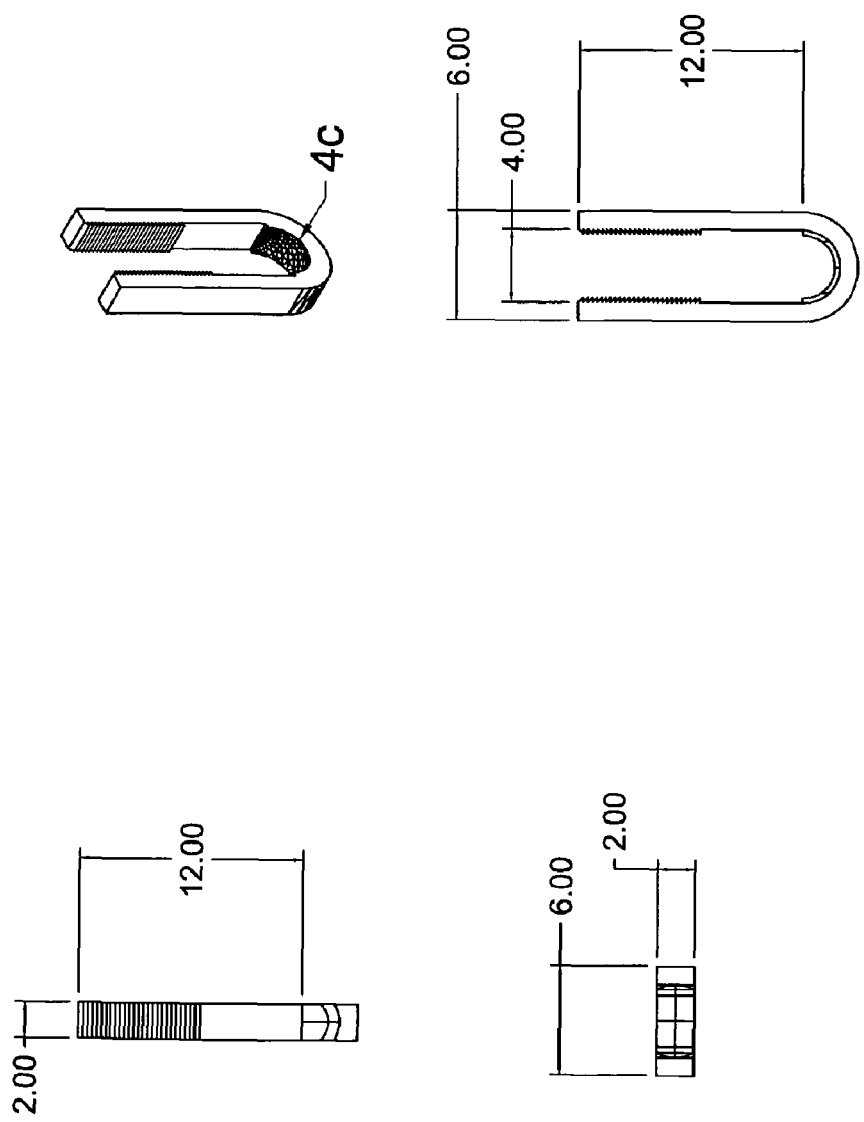
FIG. 5 shows various views of a U-shaped tension strap, with a smooth portion for passage around a ball-shaped member, such as the ball-shaped member (2c) shown in FIGS. 1-4, and retention of the rod, and a portion having a plurality of transverse ridges to engage the capture member. In various embodiments, the tension strap has a smooth first portion for passage through the channel between the connector base body and the ball-shaped member. The smooth first portion of the tension strap may be of uniform cross-section, or may employ a varying cross-section (e.g. a bulge or triangular cross-section) to enhance capture of the support member or to satisfy mechanical strength considerations. The upper sections of the tension strap may have latitudinal ridges. The latitudinal ridges on the upper sections of the tension strap may be uniform, or may be upturned or otherwise directional jagged ridges. Alternatively, the upper sections of the U-shaped strap may have latitudinal grooves or have no grooves at all.
Figure 6A:
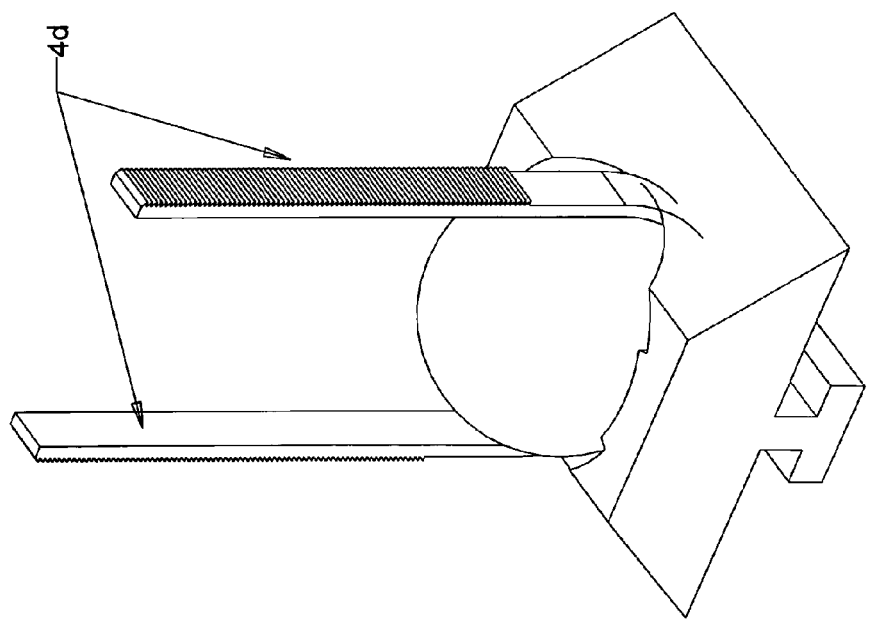
FIGS. 6a-6d show an embodiment in which the U-shaped tension strap is affixed to the connector base by various means (e.g. by welds, studs, pins, hooks, or lips). Alternatively.
Figure 6B:
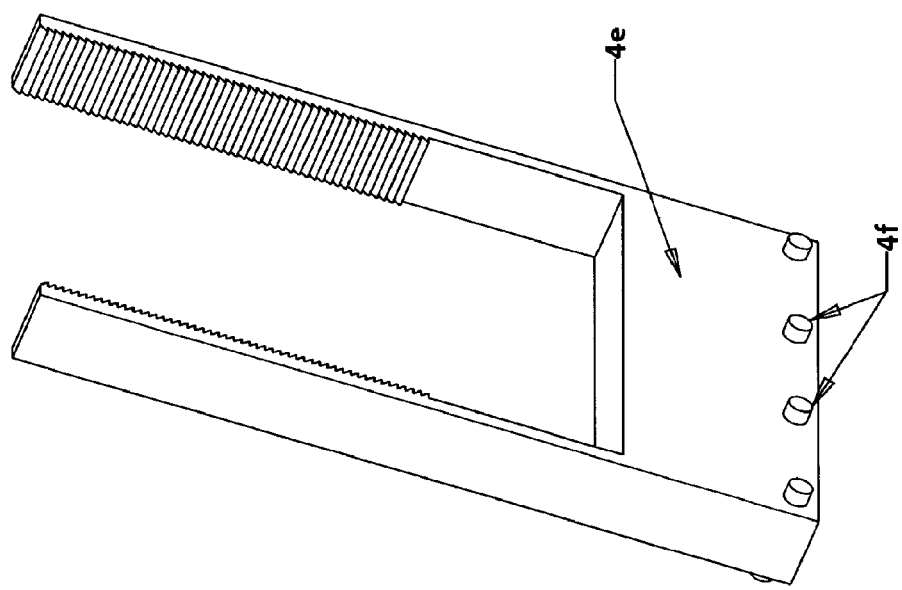
Figure 6C:
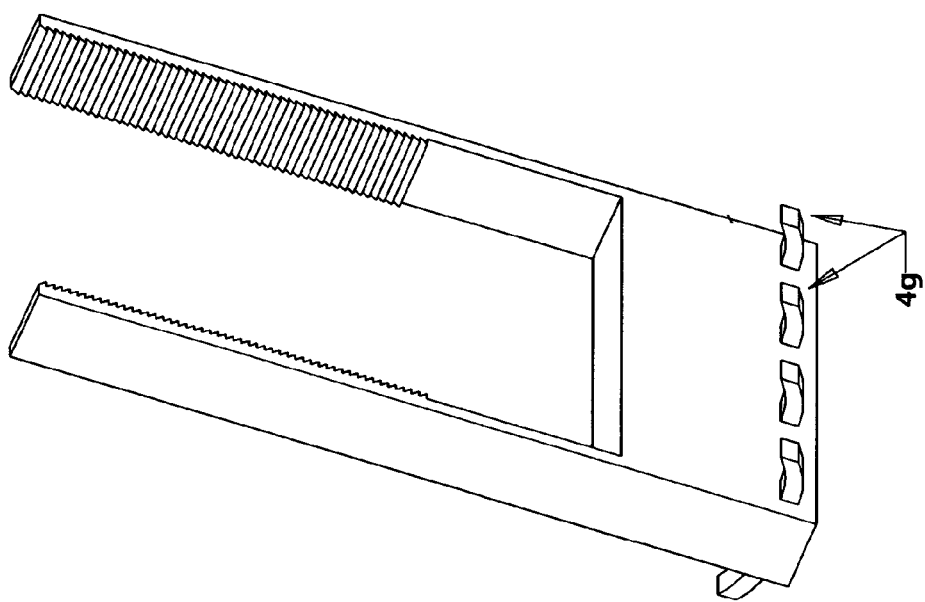
Figure 6D:
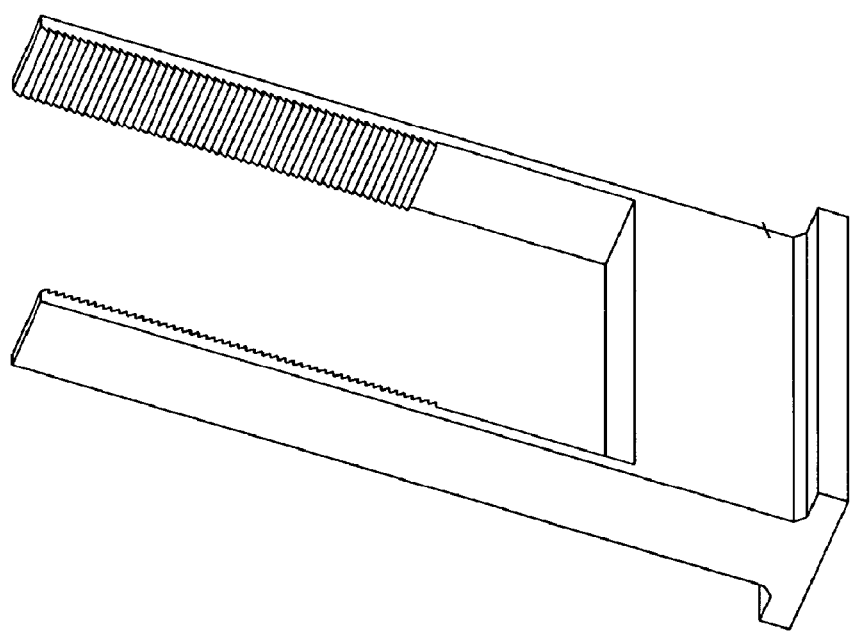
Figure 7A:
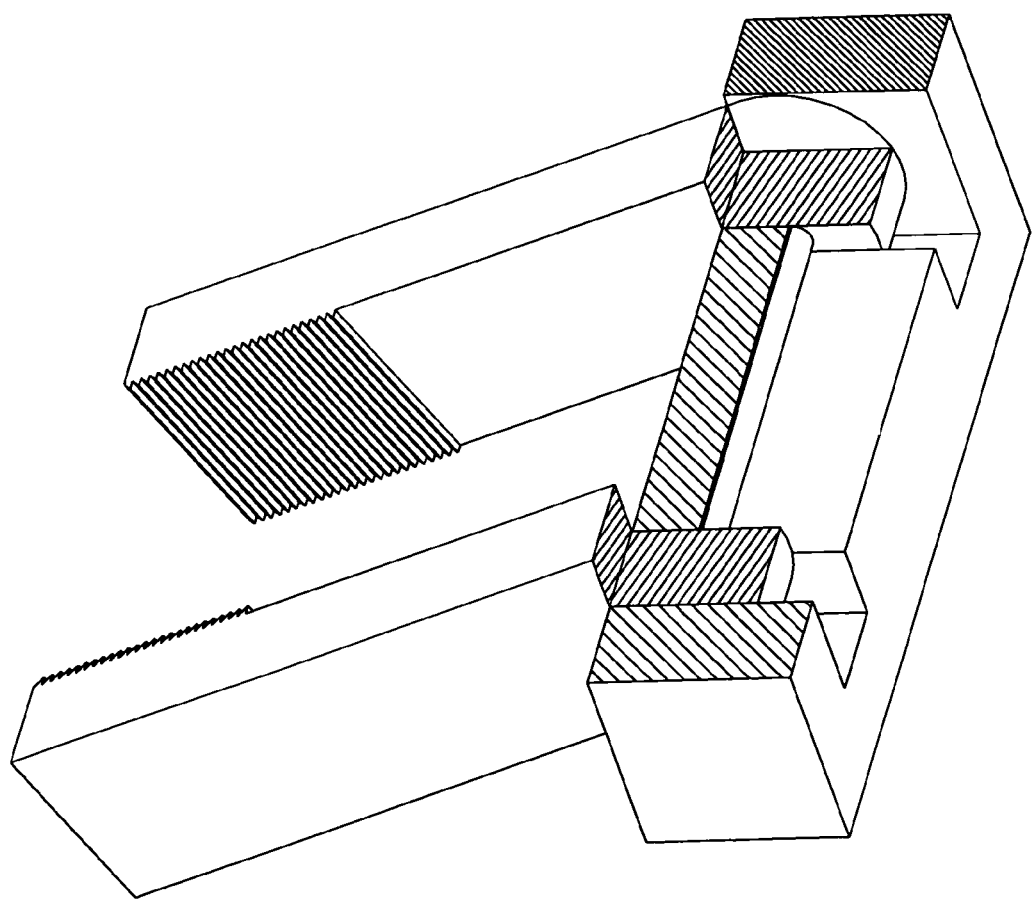
(FIG. 7a) For example, relative to a standard Cartesian coordinate system, rotation about the z-axis is represented by a cylindrical strap moving within a cylindrical channel.
Figure 7B:
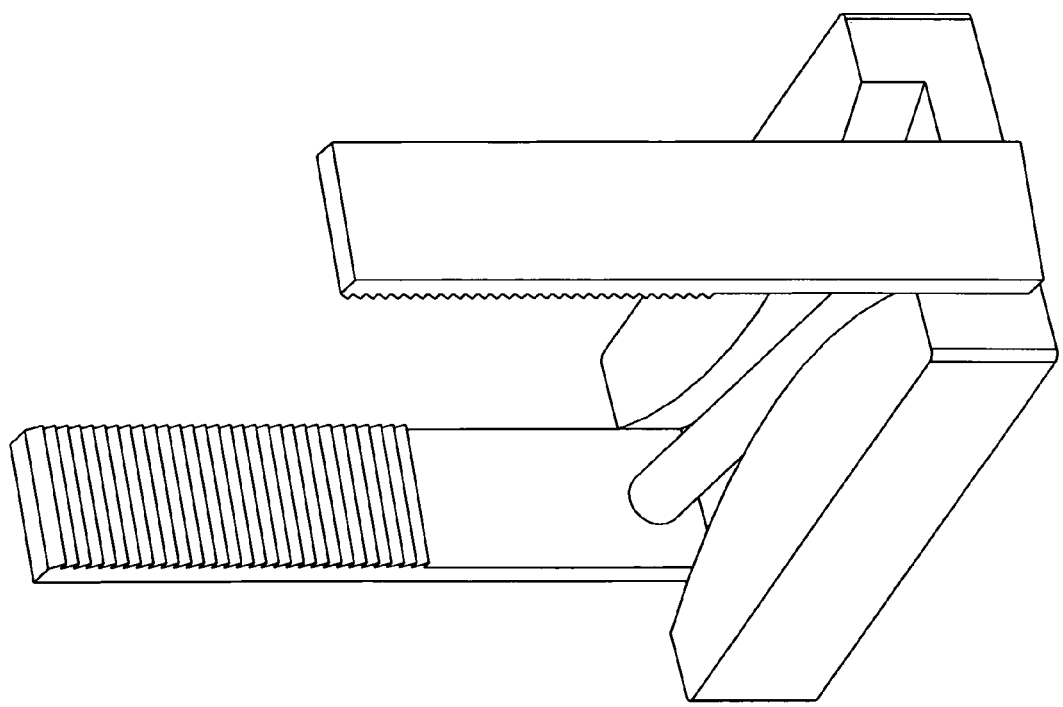
(FIG. 7b) Rotation about the y-axis is illustrated in the figure by an hour-glass shaped slot.
Figure 7C:
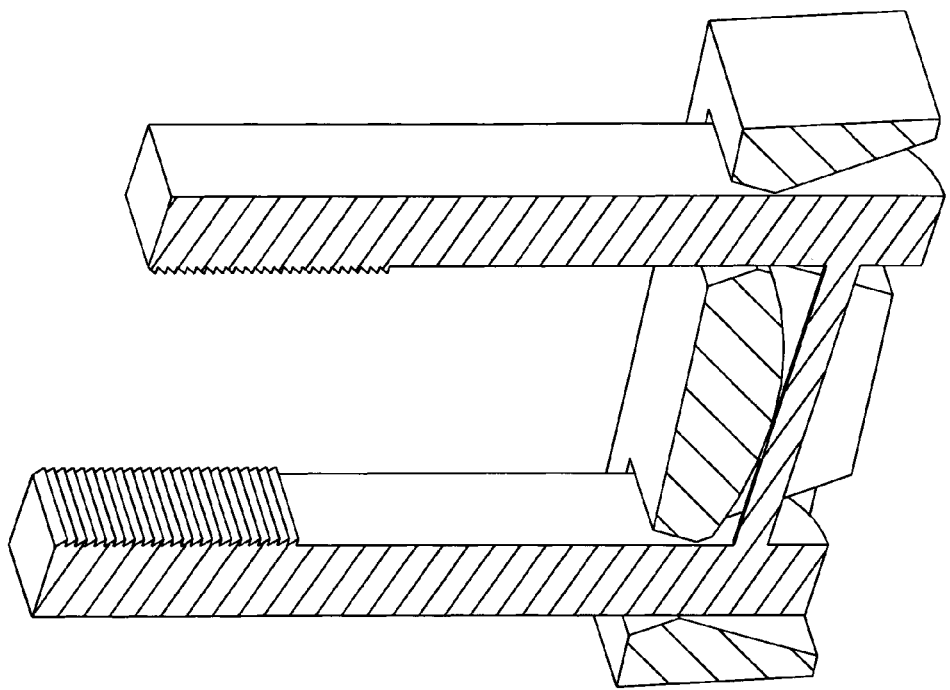
(FIG. 7c) Rotation about the x-axis is illustrated in the figure by a saddle-shaped slot (FIG. 7d) A combination of any of the aforementioned systems will allow for multi-axial motion within a specific range for each degree of freedom.
Figure 7D:
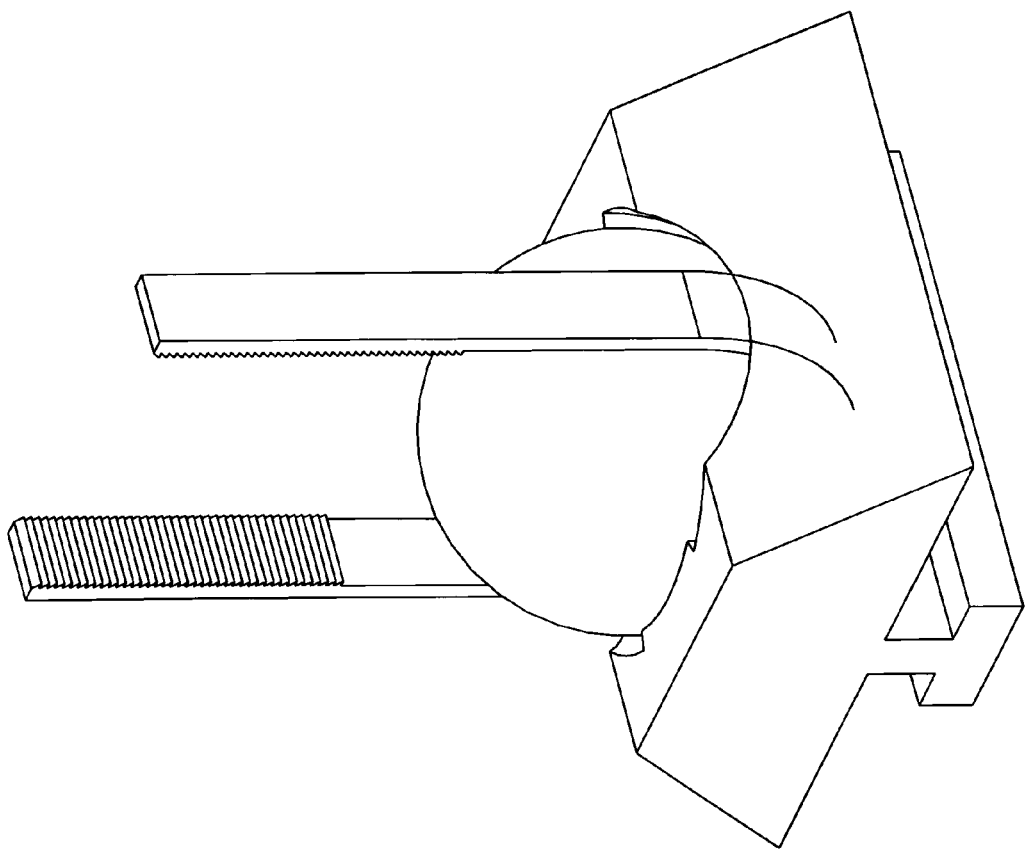
FIG. 7 shows an alternate embodiment of the tension strap which may move within a channel disposed between a ball-shaped member and a connector base body. The degrees of freedom of movement of the tension strap within the channel are dictated by the cross-sectional shape of the tension strap relative to the shape of the channel.

An interface between the ball-shaped member and the U-shaped strap [FIG. 6a, FIG. 6b, (4e)] may be characterized by pins or studs on various sides and in various configurations [FIG. 6b, (4f)]. Alternatively, the interface may be characterized by hooks [FIG. 6c, (4g)], which may be in various shapes and configurations, or by lips [FIG. 6d], which may be of various shapes and configurations. The surfaces [FIG. 6a, (4d)] of the U-shaped straps may be toothed, frictional, or smooth.

Figure 8:
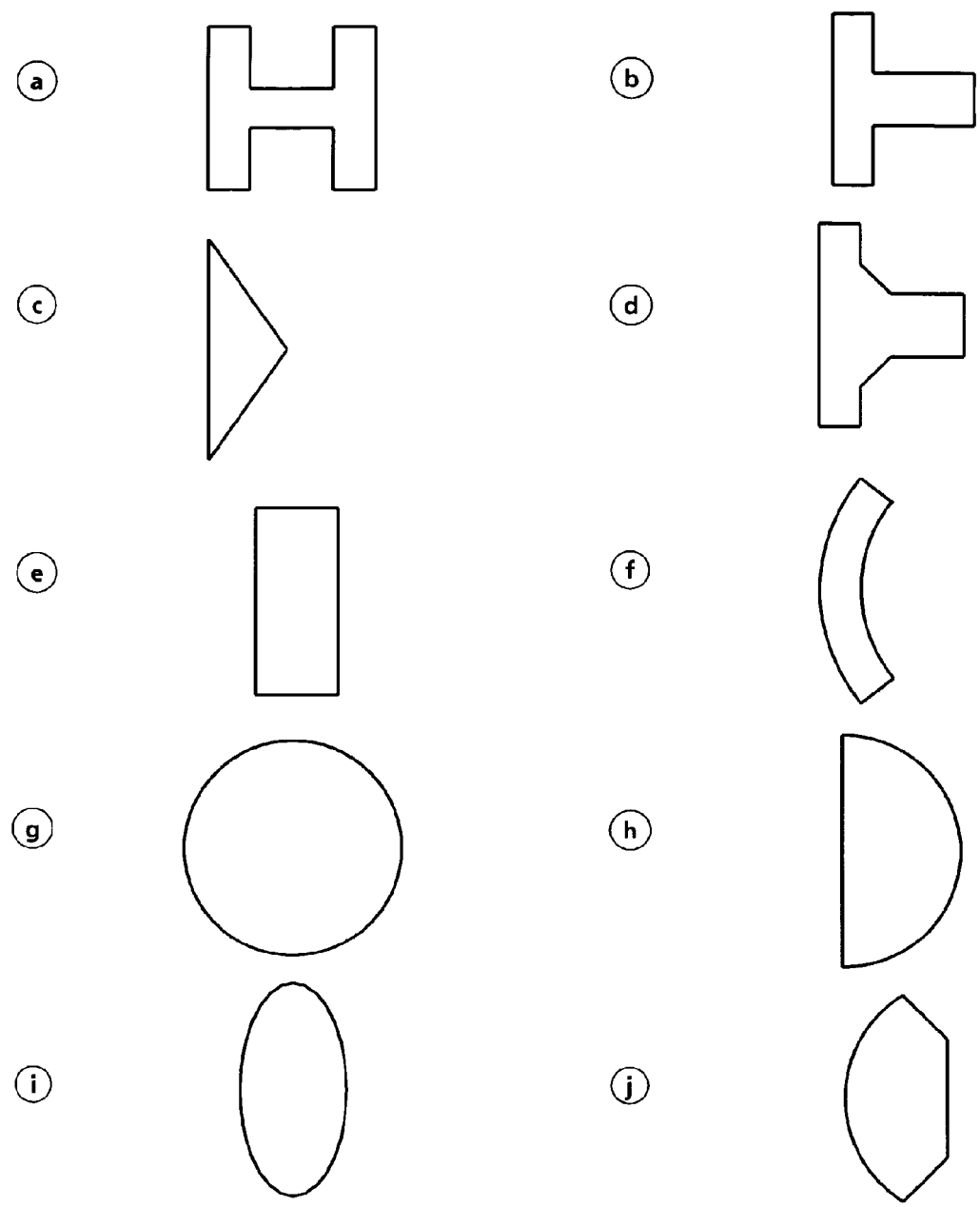
FIG. 8. Although the tension strap has been shown with a rectangular cross-section in the preceding drawings it may have various cross-section shapes, including (a) I-beam, (b) T-beam, (c) triangular, (d) gusseted, (e) rectangular, (f) curved, (g) circular, (h) half-round, (i) elliptical, or (j) a combination.

The cross-sectional shape of the U-shaped strap is generally shown in the Figures as rectangular. However, as shown in FIG. 8, it may be shaped as an (a) I-beam, (b) T-beam, (c) triangle, (d) gusseted, 9e) rectangular, (f) curved, (g) circular, (h) half-round, (i) elliptical, or (j) any combination thereof. Alternatively, the tension strap can be in configurations other than a U-shaped member with one or multiple tensioned members. Furthermore, the cross-sectional shape of the U-shaped strap may change along the longitudinal axis of the tension member, and may include special features to engage or otherwise interface with other parts of the system.

Figure 9A:
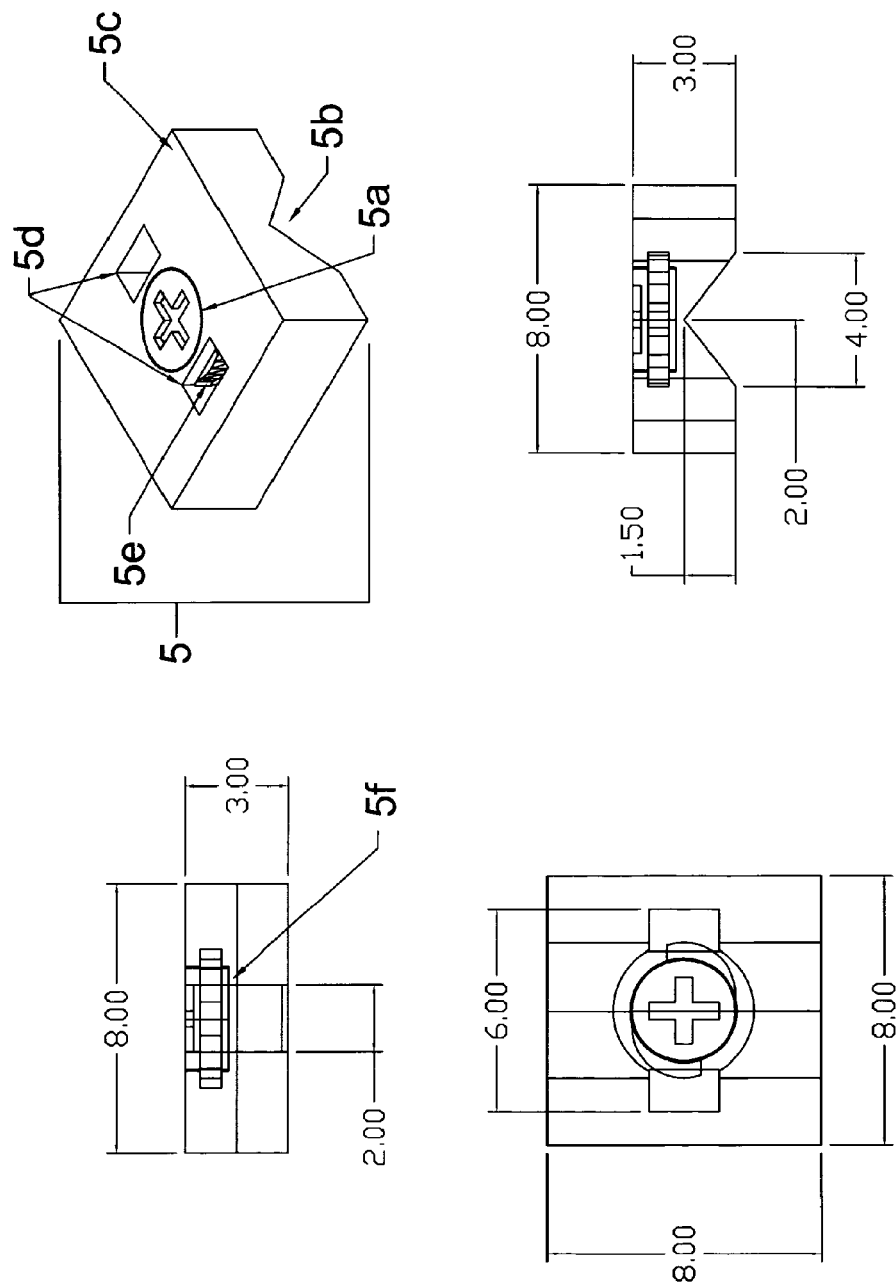
FIG. 9a shows various views of the capture member (5) with a cam lock in place (5a), a first V-shaped surface (5b), a second surface (5c), and first holes or slots therethrough (5d) with transverse grooves (5e) on an interior side of the holes or slots and a locking module (5f). In various embodiments, the first set of holes or slots in the capture member may have grooves on the interior sides of the holes or slots that are complementary to the ridges of the upper section of the U-shaped strap. Alternatively, the first set of holes or slots in the capture member may have ridges on interior sides of the holes or slots that are complementary to the grooves of the upper section of the U-shaped strap. The locking member of the capture member may be a cam locking mechanism (FIG. 9b). In some embodiments, the cam locking mechanism of the capture member may be a simple threaded member that contacts the interconnecting support member through the second (threaded) hole of the capture member. Alternatively, the cam locking mechanism, when threaded through the second hole, may tighten any deformable material that function as a disc-shaped spring that engages the transverse ridges of the U-shaped strap (see FIG. 9c). In yet another embodiment, a two-dimensional wedge of the locking screw may be employed to engage the transverse ridges of the U-shaped strap (see FIG. 9d). These latter two embodiments may be combined, i.e. the wedge of the set screw may be of the deformable material. In another embodiment, there may exist an elastic member that functions as a one- or two-dimensional spring (FIG. 9e).
Figure 9B:
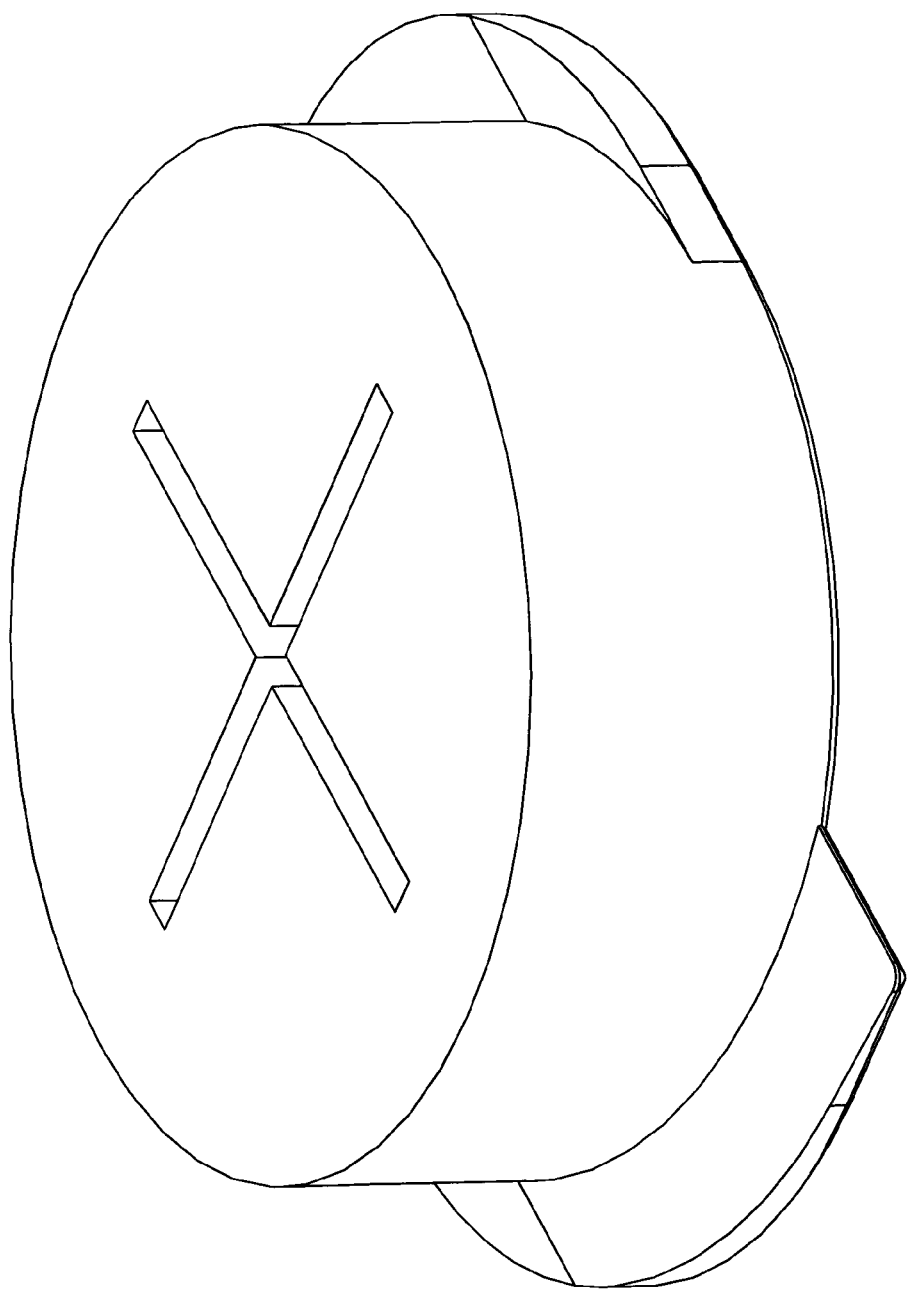
Figure 10A:
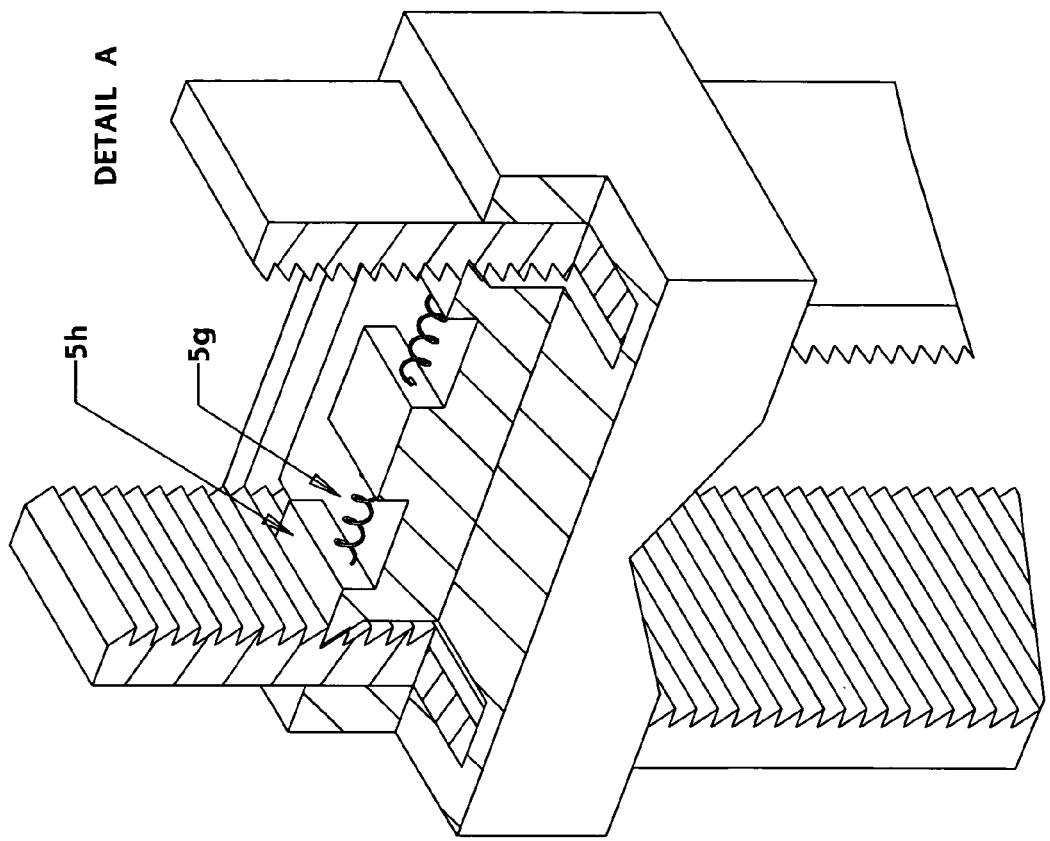
FIG. 10a shows an interior view of three embodiments of the first holes or slots (5d) in which (FIG. 10a) a spring (5g) may be used to drive a chock or wedge (5h) against the strap (tension member)
Figure 10A:
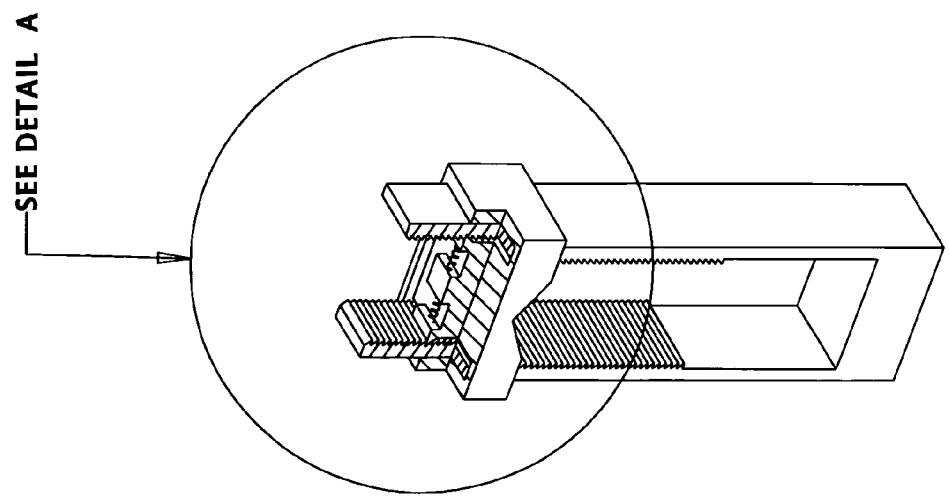
Figure 10B:
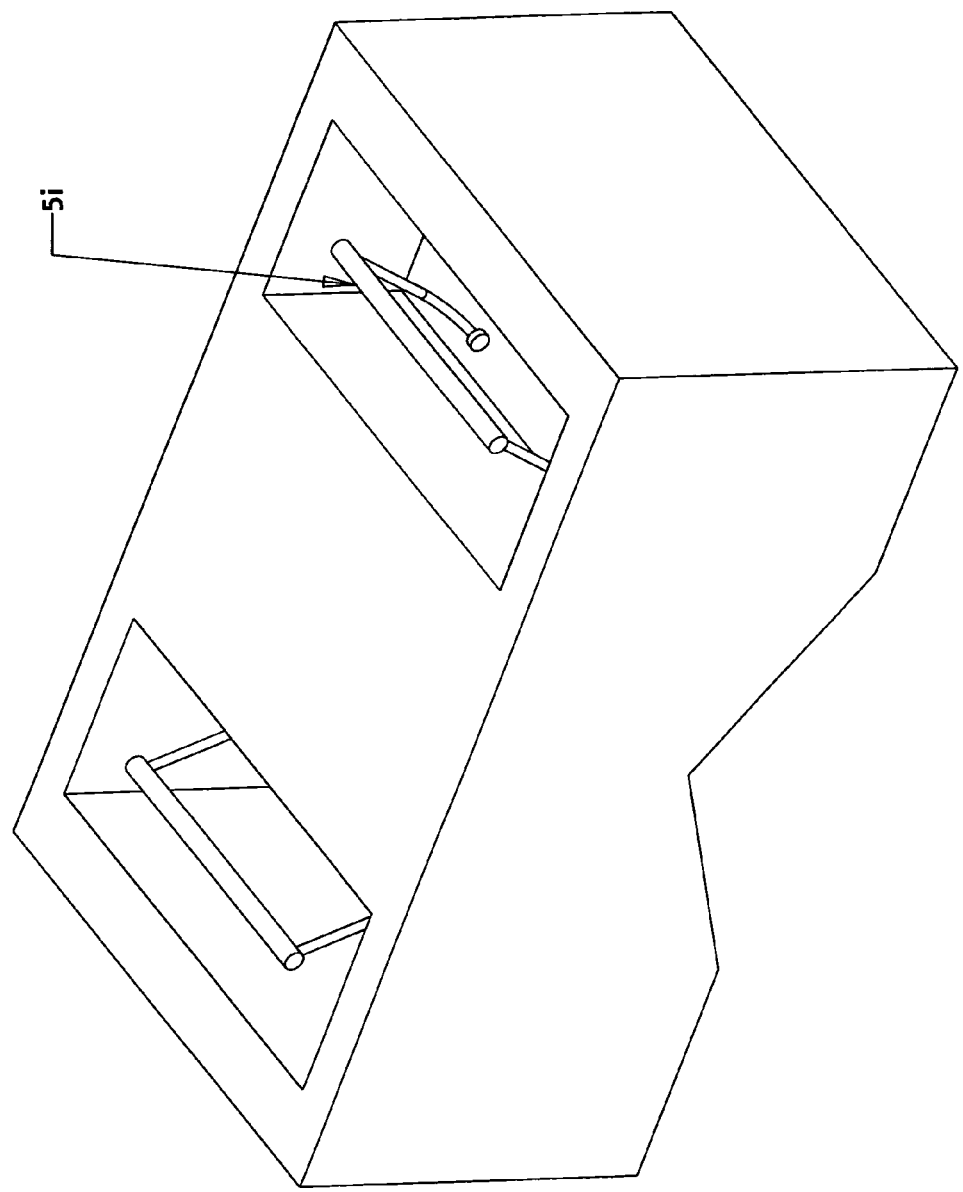
(FIG. 10b) a ball (5i) may engage the strap.
Figure 10C:
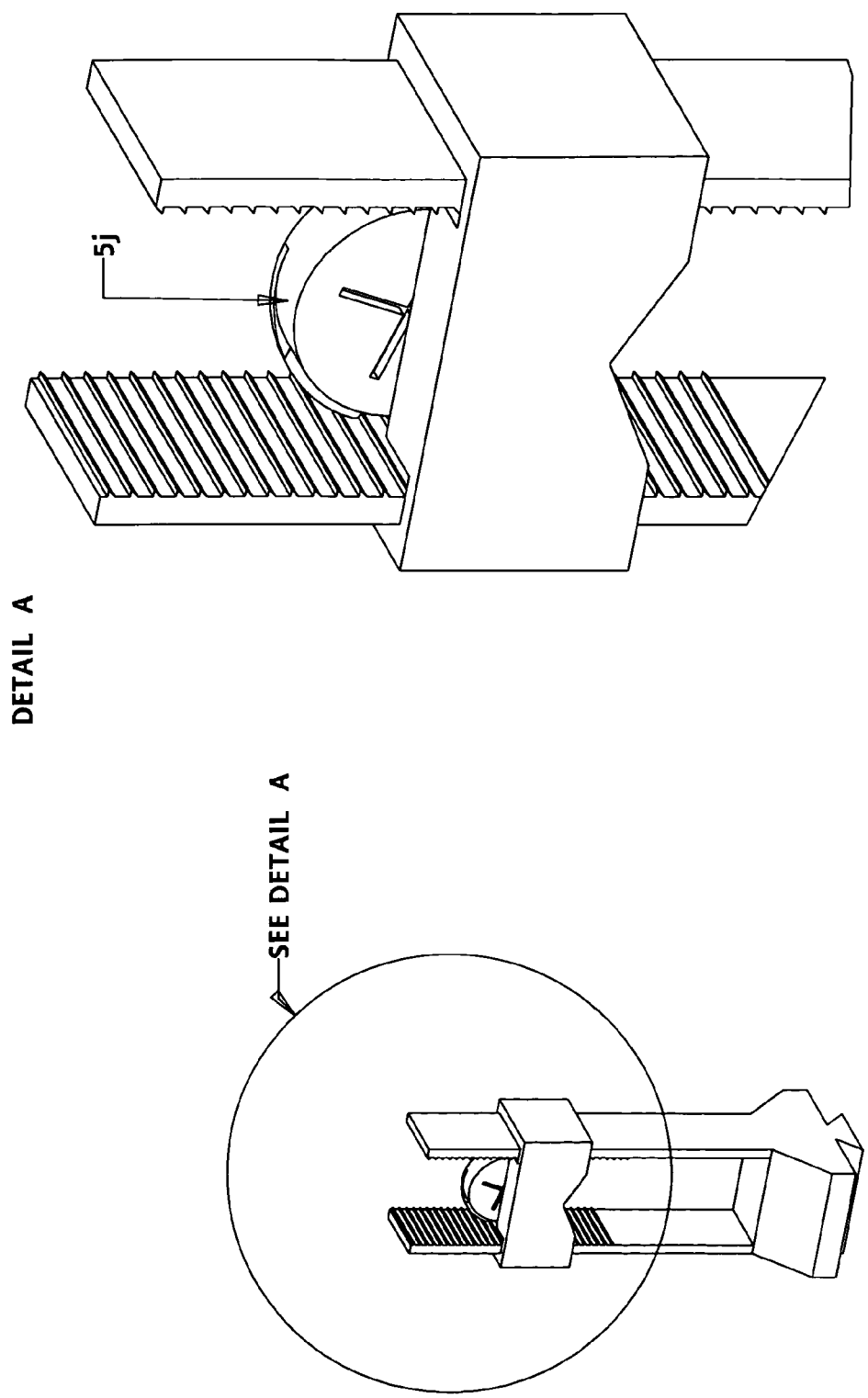
(FIG. 10c) a rotational member (5j) engages the strap in an offset cam fashion.

In the top section of the capture member [FIG. 9a, (5)], within the holes through which the U-shaped strap passes [FIG. 9a, (5d)], the strap may be secured by a wedge or chock [FIG. 10a, (5h)] driven by a spring [FIG. 10a, (5g)], which may be a coil-type, leaf-type, rotary type, or other suitable type of spring. Alternatively, the strap may be secured by a ball in an offset cam [FIG. 10b, (5i)], which may be spherical, a right circular cylinder, or other suitable shape, and which may optionally employ a spring to enhance capture. In another alternative embodiment, the strap may be secured by a rotational member [FIG. 10c, (5j)] which may optionally employ a spring to enhance capture, and which may optionally work in an offset cam fashion.

Figure 12:
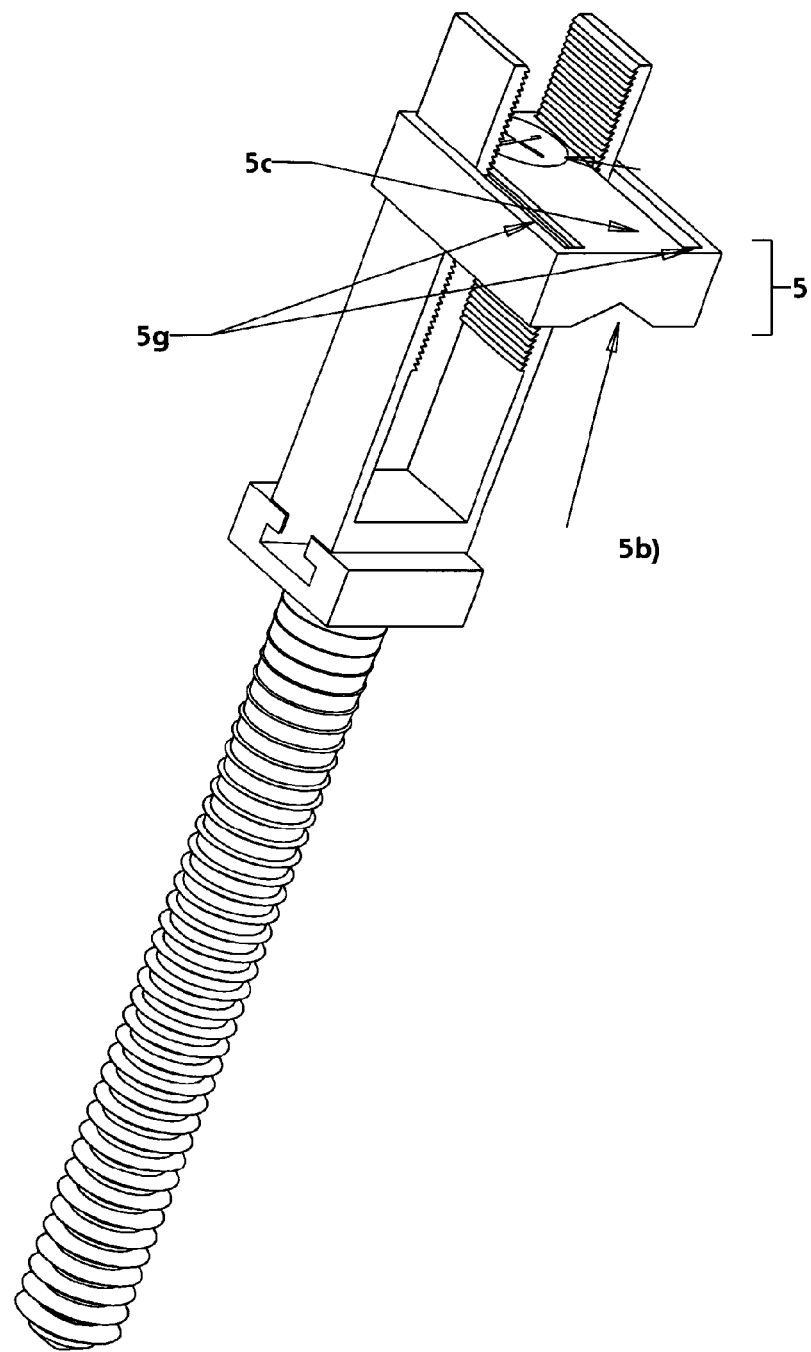
FIG. 12 shows an alternative embodiment of an apparatus according to the invention, in which the top section of the capture member (5) is an elongated beam element with a cam lock in place (5a), a first V-shaped surface (5b), a second surface (5c), and slots therethrough (5g). In this embodiment, the elongated beam element is the structural member, with no need for a rod. The elongated beam element is integral with the capture mechanism, and the unit is capable of interfacing with multiple bone anchors, thereby eliminating the need for a separate rod and further reducing the height profile of the overall assembly in the patient. In addition to the cam lock (5a), various locking mechanisms may be used that slide or otherwise move along the beam element. Although a V-shaped surface (5b) is shown in FIG. 12, the beam element may take other cross-sectional shapes, such as an inverted hemisphere. Furthermore, while the apparatus is depicted with a threaded screw-type anchor, other types of anchors may also be used.

Another alternative embodiment is shown in FIG. 12. In this embodiment, the capture member (5) is an elongated beam element with a cam lock in place (5a) a first V-shaped surface (5b), a second surface (5c) and slots therethrough (5g). In this embodiment, the elongated beam element is the structural member, with no need for a rod.

The locking mechanism incorporates the tensioning member to fix the structural member to the bone anchor with a minimum of 3 points of fixation. The ball-shaped member of the connector base represents one embodiment of this general concept. The ball may be incorporated on the bone anchor, structural member, or locking cap. The ball-shaped member of the connector base may, in various embodiments, be spherical in shape, as shown in the drawings, or may be elliptical or cylindrical, any of which may be dimpled to allow for discrete points of fixation to the rod member, as long as it allows passage of the smooth shaped portion of the U-shaped strap around it. In preferred embodiments, the ball-shaped member may be of a deformable memory shape which allows infinite dimple points of fixation to the rod member. The ball-shaped member may be integral with the connector base, i.e. of the same casting, or may be secured to the capture member, e.g. by pins or other attachment means. Those skilled in the art will recognize that any point of contact between the connector base body and the support or structural member may equivalently be substituted for the ball shaped member (see, e.g., FIG. 6e).

Figure 9C:
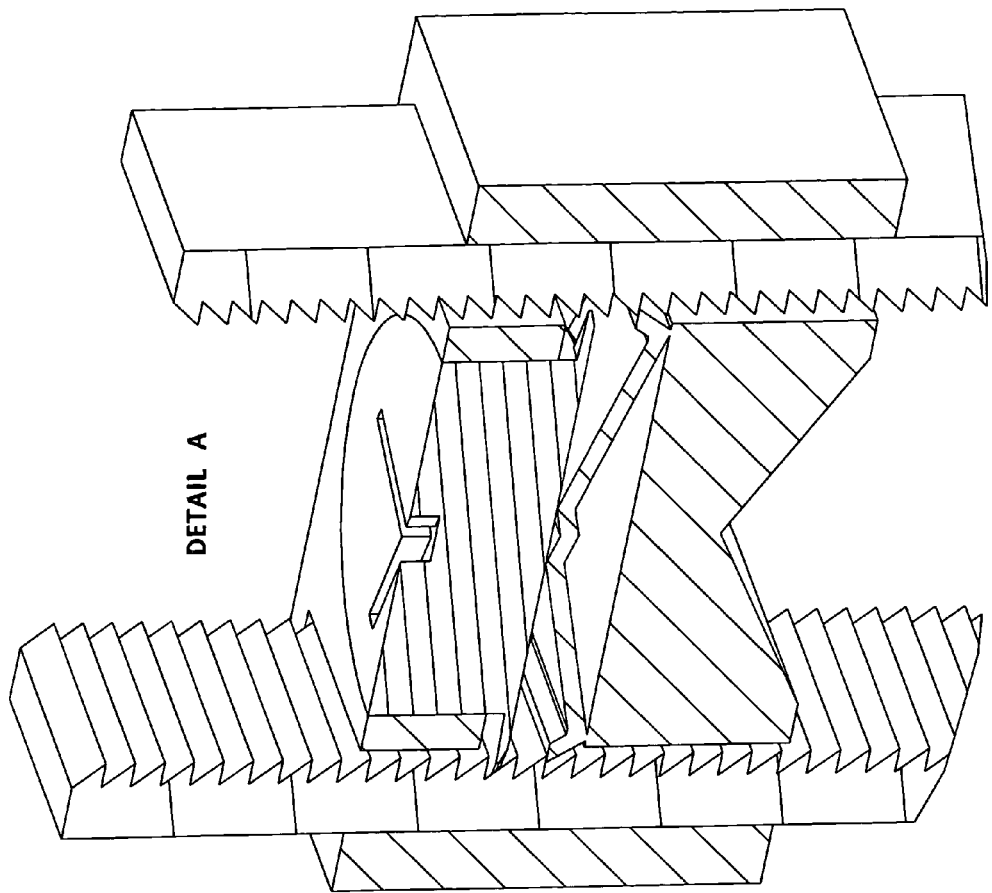
Figure 9C:
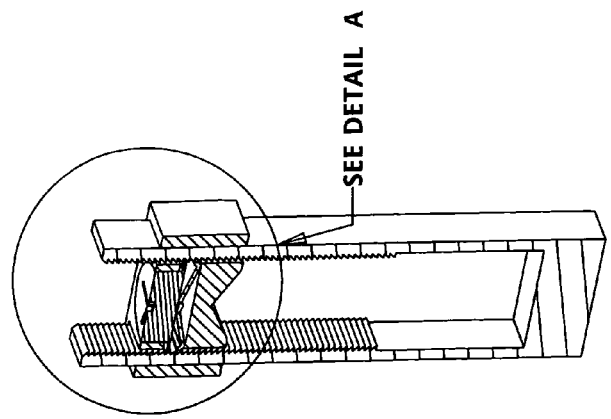
Figure 9D:
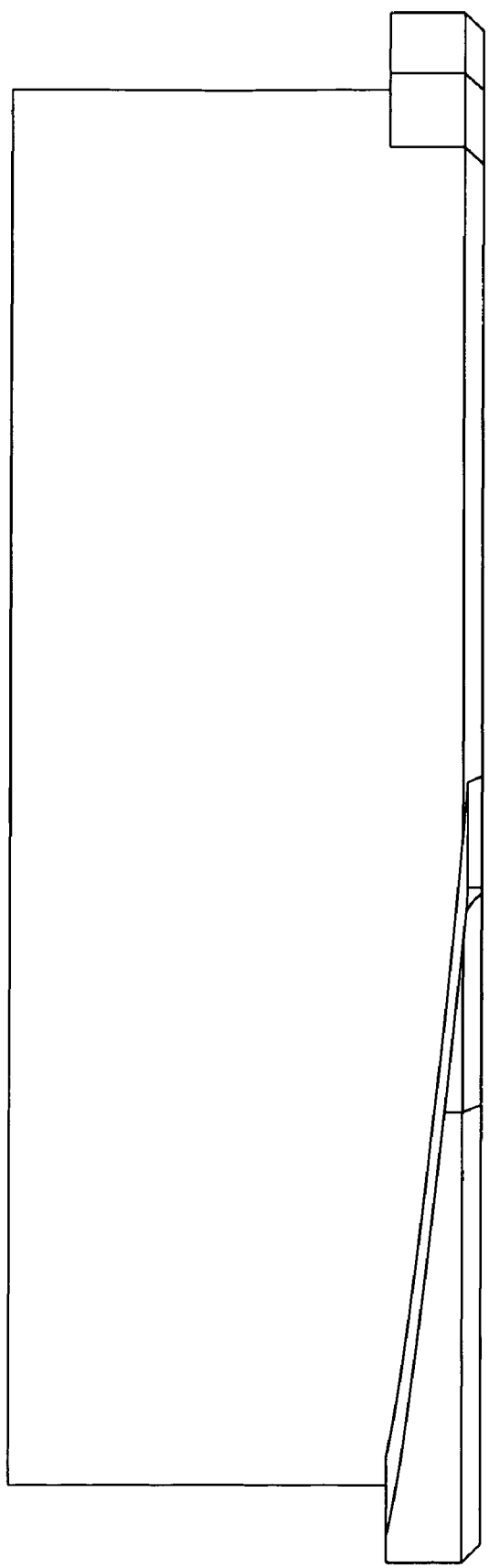
Figure 9E:
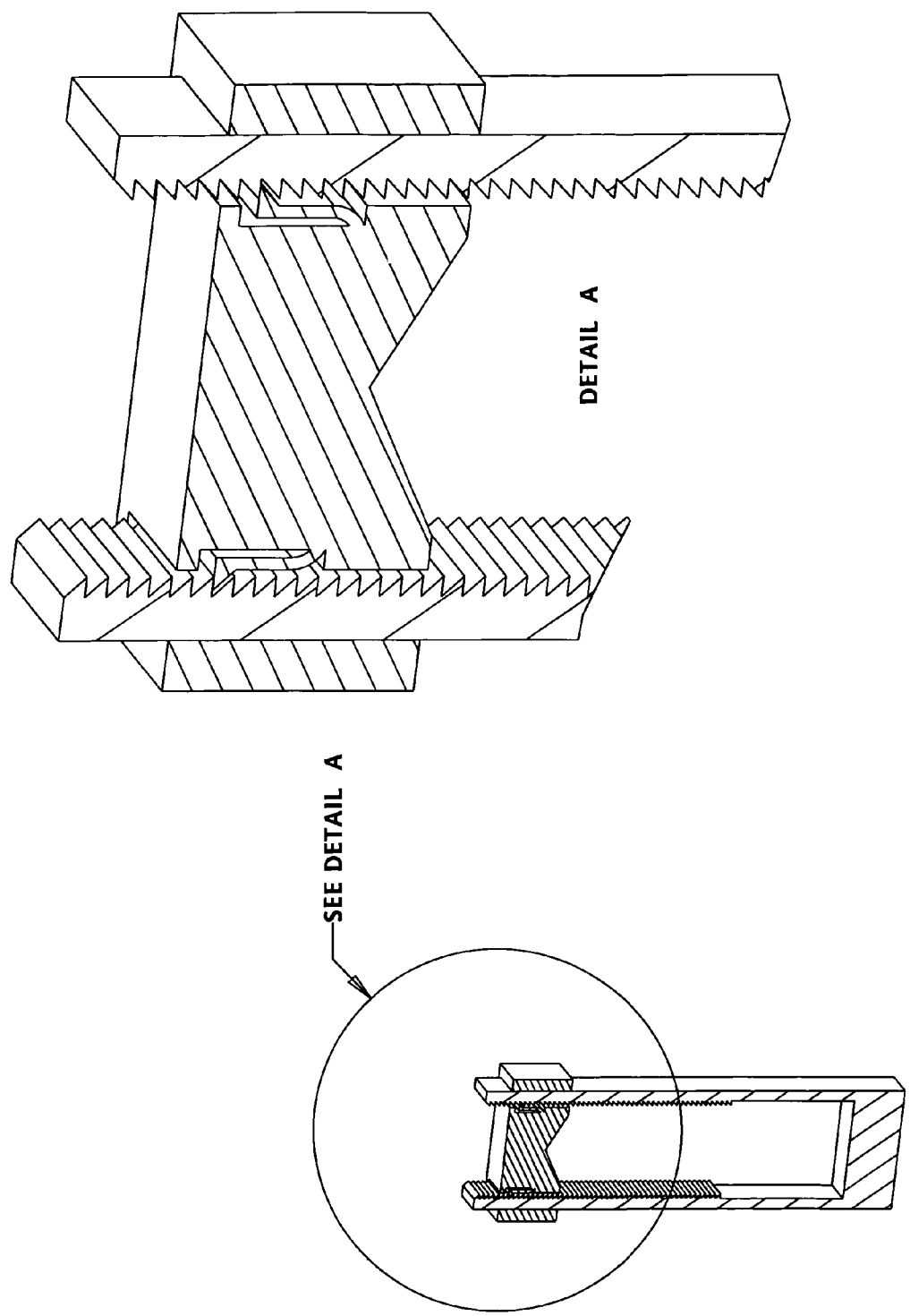

In some embodiments, the set screw of the capture member may be a simple threaded set screw that contacts the rod through the second (threaded) hole of the capture member. Alternatively, the set screw, when threaded through the second hole, may tighten a deformable memory alloy disc-shaped spring that engages the transverse ridges of the U-shaped strap (see FIG. 9c). In yet another embodiment, a two-dimensional wedge of the locking screw may be employed to engage the transverse ridges of the U-shaped strap (see FIG. 9d). These latter two embodiments may be combined, i.e. the wedge of the set screw may be of the deformable memory alloy material.

Materials for the various components of the system may be any of those conventionally used for spinal fixation systems, or any other materials having proper mechanical properties.

In a second aspect, the invention provides a method for fixation of a bone anchor to a structural member of a spine fixation system whereby the spine is provided mechanical stability and correction of deformity through load carried fully or partially through the structural member. The method according to this aspect of the invention comprises affixing a bone anchor to a vertebra, the bone anchor comprising means for attachment to the bone and a connector base comprising a body, a ball-shaped member, and a channel between the body and the ball-shaped member; passing a U-shaped strap through the channel in the connector base, placing a structural member within the U-shaped strap, inserting a top section of a capture member over the U-shaped strap; and drawing the top section of the capture member under tension over the structural member until the structural member contacts the ball-shaped member at the base of the capture mechanism, creating a minimum of 3 points of compressive fixation between the structural member, the locking cap, and the connector base.

To assist in the reduction of the locking cap, a tensioning device is secured to the free ends of the tension band. An upward force is applied to the ends of the tension band while the locking cap is simultaneously pushed downward along the tension band until it encounters the structural member. By applying sequential tension, the locking cap forces the structural member to rigidly engage the ball shaped member of the connector base, while the tension band simultaneously rigidly engages the opposing surface of the ball shaped member (FIG. 11). The locking cap, in combination with the tension band and bone anchor, forms an integral part of the reduction maneuver when the system is being used to correct deformity. The reduction tool secures the ends of the tension strap using wedges, collets, pliers, claws, hooks, or any other suitable means of attachment. The reduction tool also captures the locking cap using slots, wedges, springs, or any other suitable means for holding the cap to maintain it in proper orientation as it is advanced downward along the tension strap to engage the structural member. The reduction tool is calibrated to apply a critical force that stabilizes the entire construct (locking cap, tension band, structural member, and connector base) sufficiently to resist loosening, slippage, or micromotion.

What is claimed is:
1. A spinal fixation system comprising:
a support member;
a plurality of fixation members connected by the support member, wherein each fixation member comprises
an attachment member configured to be attached to a vertebra and a docking member, a connector base attached to the docking member and having a first body, a ball-shaped member disposed within the first body, and a channel disposed between the ball-shaped member and the first body, a tension strap arranged within the channel and around the ball-shaped member, the strap being configured to receive the support member, and a capture member comprising a second body having a lower surface and an upper surface, the second body having first and second opposing holes configured to receive the tension strap and a third hole configured to receive a cam lock, wherein the lower surface of the second body and the ball-shaped member of the connector base provide three points of fixation with the support member.

2. The apparatus according to claim 1, wherein the support member is a rod or a wire disposed within the tension strap between the ball shaped member and the lower surface of the capture member.

3. The apparatus according to claim 1, wherein an interface between the ball-shaped member and the tension strap comprises pins, studs, hooks or lips.

4. The apparatus according to claim 1, wherein the tension strap has a cross-sectional shape selected from the group consisting of I-beam, T-beam, triangle, gusseted, rectangular, curved, circular, half-round, elliptical and any combination thereof.

5. The apparatus according to claim 1, wherein within the holes through which the tension strap passes, the strap is secured by a wedge or chock driven by a spring.

6. The apparatus according to claim 1, wherein within the holes through which the tension strap passes, the strap is secured by a ball or cylinder or an offset cam.

7. The apparatus according to claim 1, wherein within the holes through which the tension strap passes, the strap is secured by a rotational member.

8. The apparatus according to claim 1, wherein the connector base and tension strap form a unitary body.

9. The apparatus according to claim 1, wherein the cam lock is a set screw.

10. The apparatus according to claim 1, wherein the cam lock comprises a set screw that tightens a deformable material to form a disk-shaped spring that engages transverse ridges in the tension strap.

11. The apparatus according to claim 1, wherein the cam lock comprises a locking screw having a two dimensional wedge that engages transverse ridges in the tension strap.

12. The apparatus according to claim 1, wherein the channel between the ball shaped member and the body of the capture member is cylindrical.

13. The apparatus according to claim 1, wherein the channel between the ball shaped member and the body of the capture member is hour-glass shaped.

14. The apparatus according to claim 1, wherein the channel between the ball shaped member and the body of the capture member is saddle shaped.

15. A method for fixation of a bone anchor of a spinal fixation system to a structural member of the spinal fixation system, the method comprising:

affixing a bone anchor to a vertebra, the bone anchor having a connector base comprising a body, a ball-shaped member, and a channel between the body and the ball-shaped member;

passing a tension strap through the channel in the connector base;

placing the structural member within the tension strap;

inserting a capture member over the tension strap;

and drawing the capture member down over the structural member until the structural member contacts the ball-shaped member, thereby creating a minimum of three points of compressive fixation between the structural member, the locking cap, and the connector base.

16. The method according to claim 15, wherein drawing down the capture member down over the structural member comprises securing a tensioning device to free ends of the tension strap by applying an upward force to the ends of the tension strap, and simultaneously applying a downward force to the capture member until it encounters the structural member.

17. The method according to claim 16, wherein the tensioning device secures the ends of the tension strap using wedges, collets, pliers, claws, hooks, or other suitable means of attachment.

18. The method according to claim 16, wherein the tensioning device secures the capture member using an element configured for holding the capture member in a predetermined orientation as it is subjected to the downward force.

19. The method according to claim 18, wherein the element configured for holding the capture member comprises one or more slots, wedges, springs or any combination thereof.

20. The method according to claim 16, wherein the upward force is applied using one or more wedges, collets, pliers, claws or hooks.

* * * * *